US012150648B2

United States Patent
Walsh

(10) Patent No.: US 12,150,648 B2
(45) Date of Patent: Nov. 26, 2024

(54) STRUT FLOW DIVERTER FOR CEREBRAL ANEURYSMS AND METHODS FOR PREVENTING STRUT ENTANGLEMENT

(71) Applicant: DePuy Synthes Products, Inc., Raynham, MA (US)

(72) Inventor: Michael Walsh, Foster City, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 362 days.

(21) Appl. No.: 17/847,688

(22) Filed: Jun. 23, 2022

(65) Prior Publication Data
US 2022/0323081 A1   Oct. 13, 2022

Related U.S. Application Data

(62) Division of application No. 16/294,027, filed on Mar. 6, 2019, now Pat. No. 11,382,633.

(51) Int. Cl.
*A61B 17/12*   (2006.01)
(52) U.S. Cl.
CPC .. *A61B 17/12113* (2013.01); *A61B 17/12145* (2013.01); *A61B 2017/1205* (2013.01)
(58) Field of Classification Search
CPC ........ A61B 17/12113; A61B 17/12145; A61B 2017/1205
See application file for complete search history.

(56) References Cited

U.S. PATENT DOCUMENTS

| | | | |
|---|---|---|---|
| 6,168,615 B1 * | 1/2001 | Ken | A61B 17/12036 |
| | | | 623/1.1 |
| 6,391,037 B1 | 5/2002 | Greenhalgh | |
| 6,589,265 B1 * | 7/2003 | Palmer | A61B 17/12022 |
| | | | 623/1.1 |
| 9,232,992 B2 | 1/2016 | Heidner | |
| 9,532,792 B2 | 1/2017 | Galdonik et al. | |
| 9,532,873 B2 | 1/2017 | Kelley | |

(Continued)

FOREIGN PATENT DOCUMENTS

| | | |
|---|---|---|
| JP | 2003-275218 A | 9/2003 |
| WO | 99/56636 A1 | 4/1999 |
| WO | 2018/051187 A1 | 3/2018 |

OTHER PUBLICATIONS

Chinese Office Action issued in corresponding Appln. No. 202010151157X, dated Jan. 18, 2024, related to U.S. Appl. No. 17/847,688, with English translation.

(Continued)

*Primary Examiner* — Sarah A Long
(74) *Attorney, Agent, or Firm* — Troutman Pepper Hamilton Sanders LLP

(57) ABSTRACT

Implants described herein can be used as flow diverters and can generally include a plurality of twisting struts extending from a central node. The twisting struts can be twisted along a long axis of each strut. The implant can have a proximal portion affixed to the central node and extending radially from the central node. The twisting struts can have a distal portion. The long axis can be disposed between the proximal portion and the distal portion of the twisting struts. The implant can have a collapsed configuration to be delivered through a catheter into an aneurysm. The implant can have an expanded configuration to anchor within the aneurysm.

16 Claims, 10 Drawing Sheets

(56) References Cited

U.S. PATENT DOCUMENTS

| | | |
|---|---|---|
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,004,510 B2 | 6/2018 | Gerberding |
| 2006/0064151 A1 | 3/2006 | Guterman |
| 2008/0281350 A1 | 11/2008 | Sepetka |
| 2010/0324649 A1 | 12/2010 | Mattsson |
| 2012/0283768 A1 | 11/2012 | Cox et al. |
| 2014/0135812 A1 | 5/2014 | Divino et al. |
| 2014/0200607 A1 | 7/2014 | Sepetka et al. |
| 2015/0238198 A1 | 8/2015 | Le et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2019/0216467 A1* | 7/2019 | Goyal .............. A61B 17/12113 |

OTHER PUBLICATIONS

Extended European Search Report issued in corresponding European Patent Application No. 20 16 1158 dated Aug. 5, 2020.

* cited by examiner

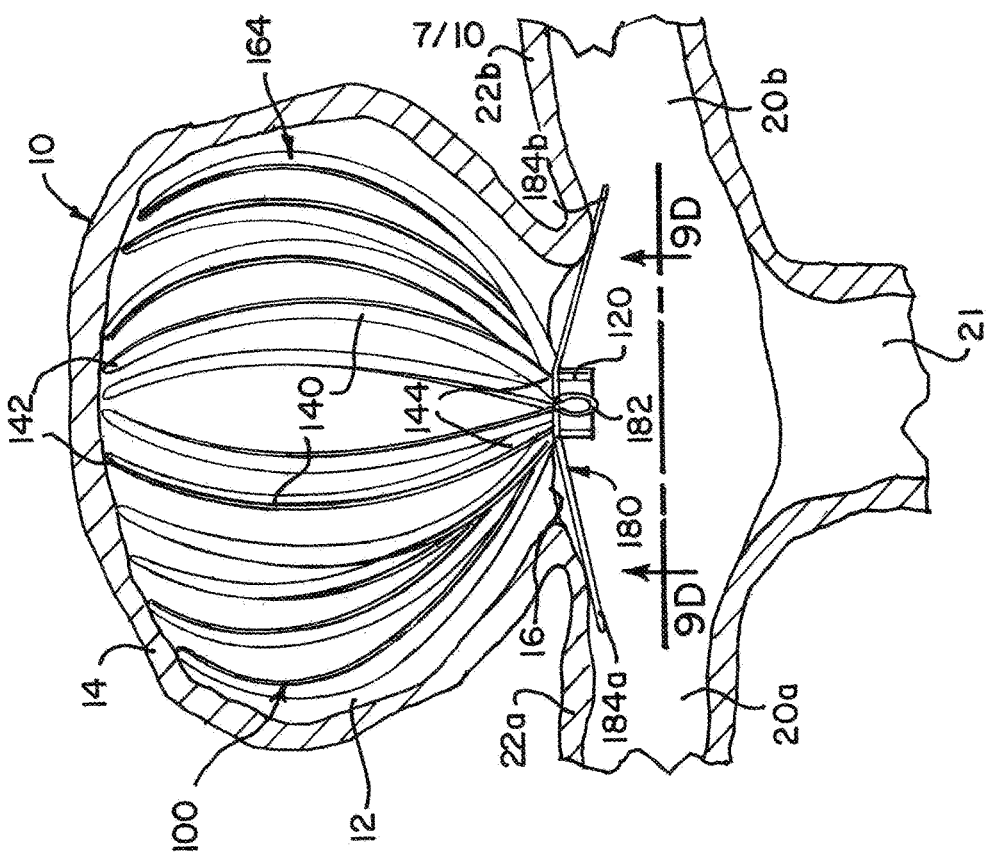
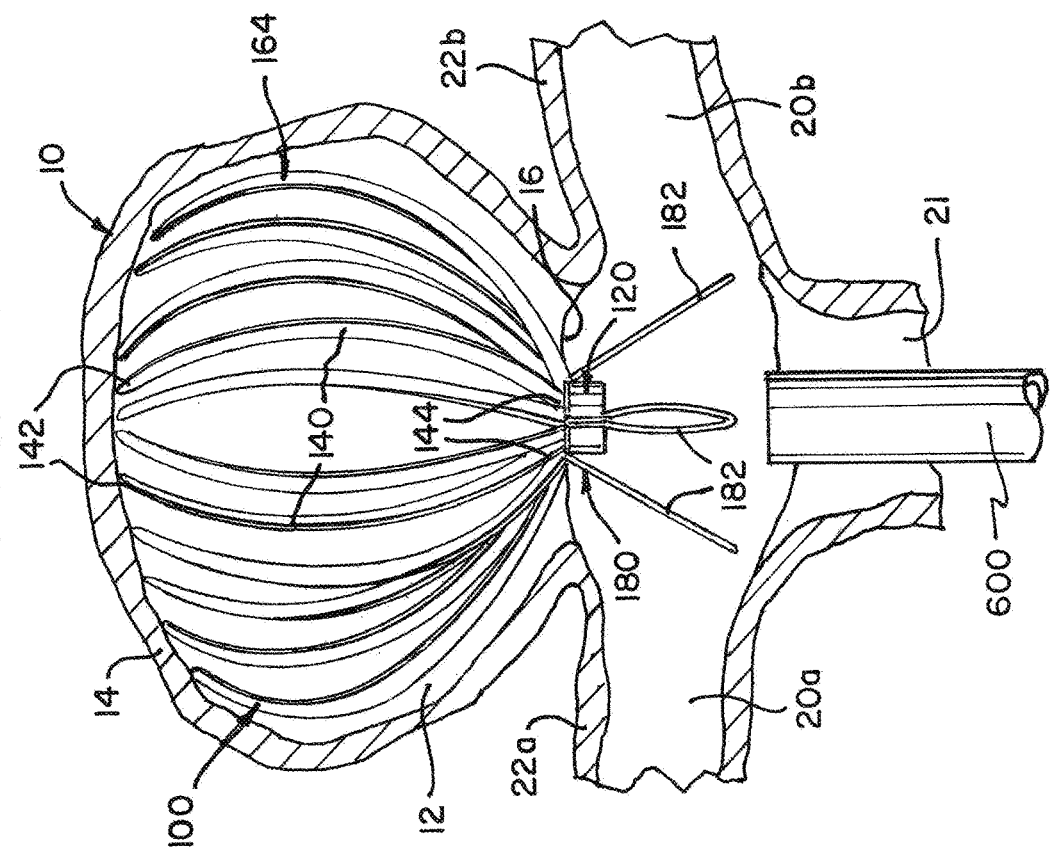

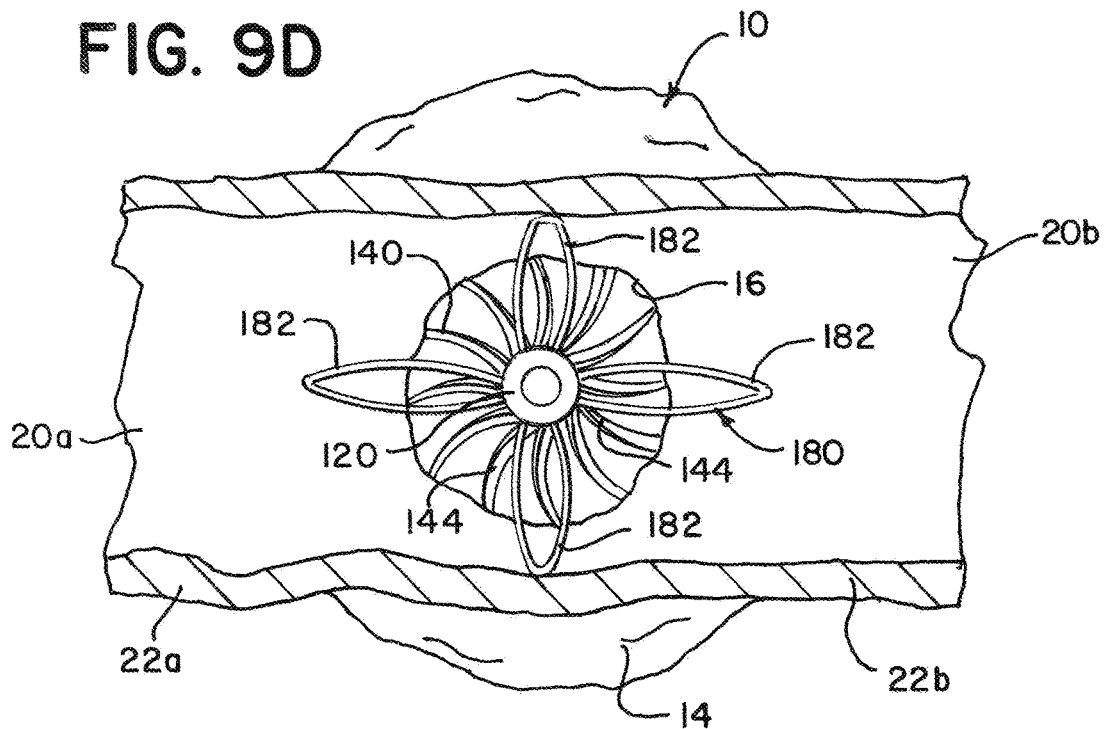
FIG. 9D
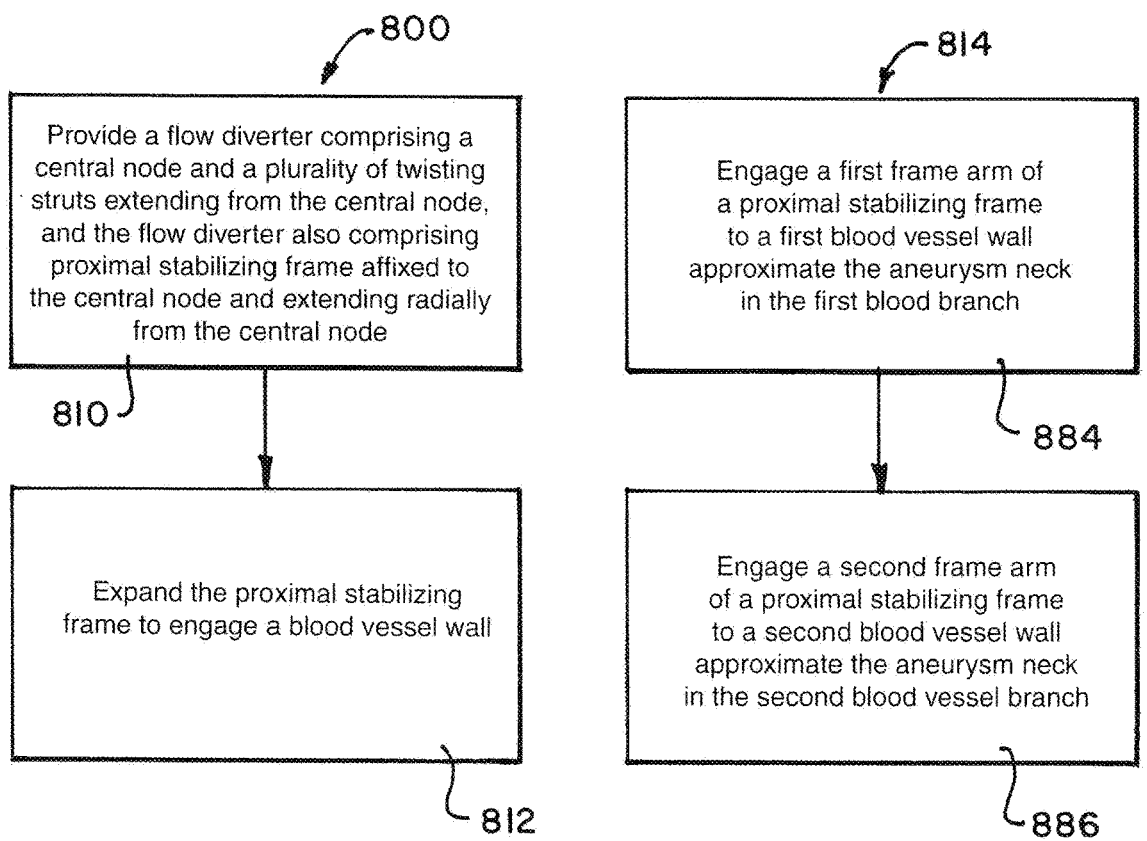
FIG. 11
FIG. 12

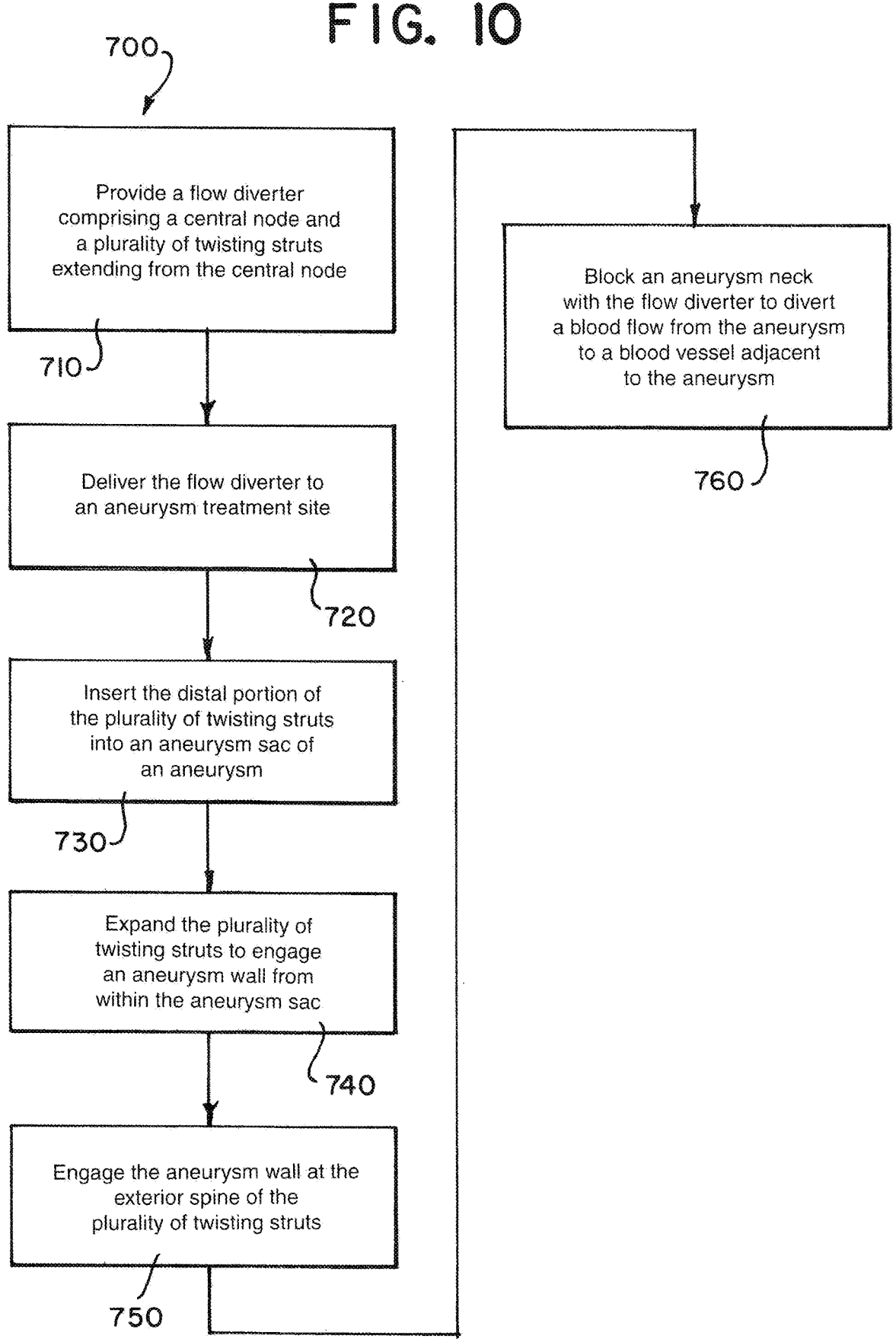

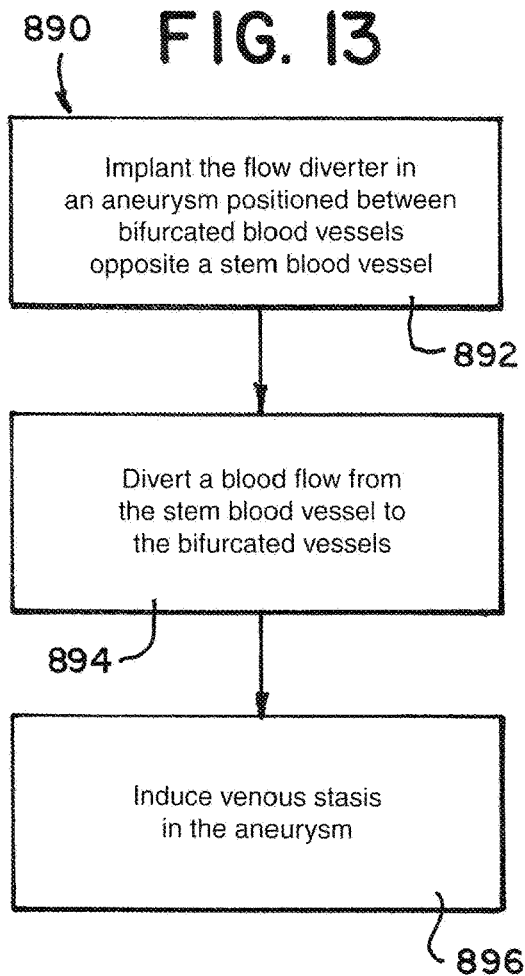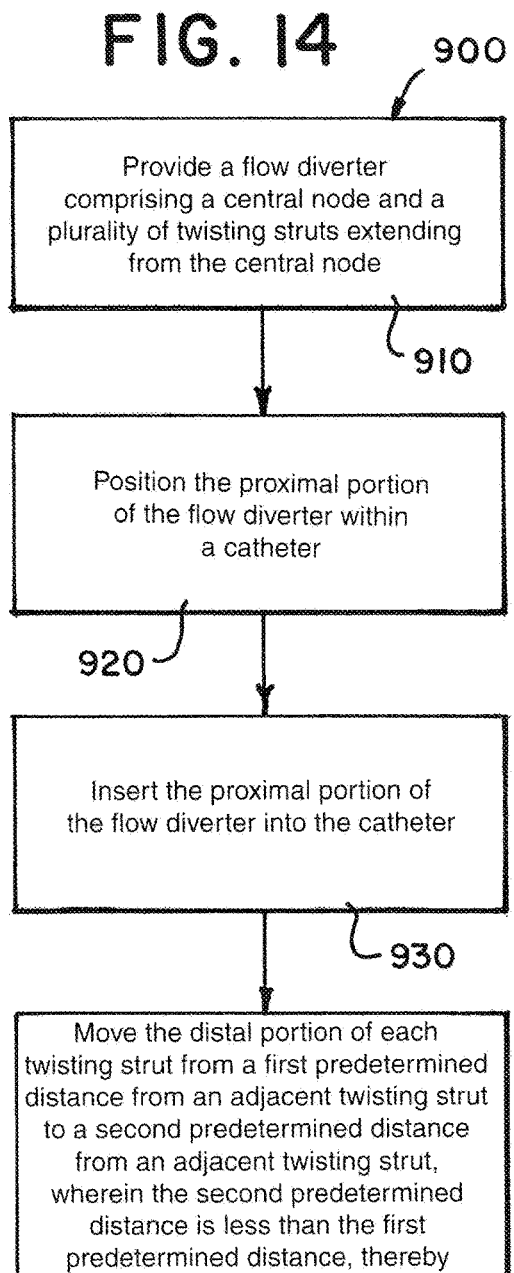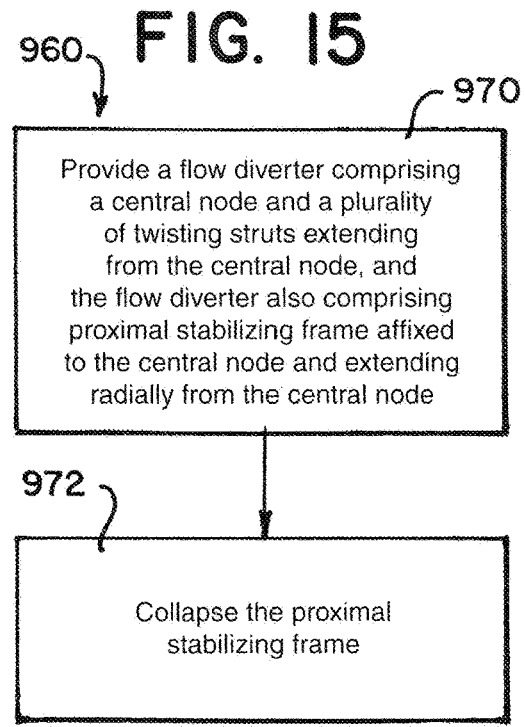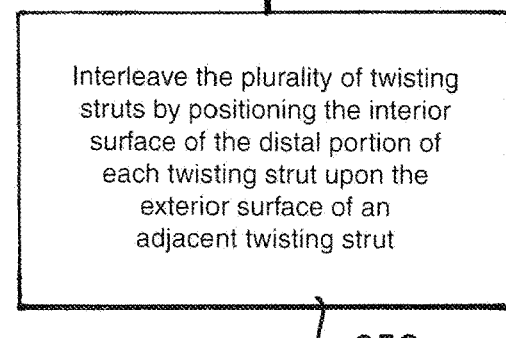

STRUT FLOW DIVERTER FOR CEREBRAL ANEURYSMS AND METHODS FOR PREVENTING STRUT ENTANGLEMENT

CROSS-REFERENCE TO RELATED APPLICATIONS

The present application is a divisional application of U.S. patent application Ser. No. 16/294,027 filed Mar. 6, 2019. The entire contents of which are hereby incorporated by reference.

FIELD OF INVENTION

The present invention generally relates to aneurysm treatment devices, and more particularly, to flow diverters.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include implanting devices that fill the sac of the aneurysm with embolic material, divert blood from the aneurysm neck, or both to prevent blood flow into the aneurysm. When filling the aneurysm sac, the embolic material clots the blood, creating a thrombotic mass within the aneurysm. When treating the aneurysm neck, blood flow into the entrance of the aneurysm is inhibited and/or diverted to flow through a blood vessel, thereby inducing venous stasis in the aneurysm and facilitating a natural formation of a thrombotic mass within the aneurysm.

Current treatments primarily include implanting a stent and/or embolic coils. A stent can be expanded within a blood vessel to extend across the neck of the aneurysm, thereby effectively diverting blood flow away from the aneurysm and through the blood vessel. However, stents are typically not viable treatment devices for aneurysms located at a bifurcation because a stent can inhibit blood flow through the vasculature at the bifurcation. Embolic coils are typically used in current treatments for packing aneurysms, and in some instances, for treating the aneurysm neck. Embolic coils, alas, are typically not viable treatment devices for wide neck aneurysms because the embolic coils can recanalize, provide poor coverage across the aneurysm neck, and/or extend into the adjoining blood vessel. Stents can be used in conjunction with embolic coils, and in such strategies, typically the embolic coils pack the aneurysm sac and the stent inhibits the coils from exiting the aneurysm. However, neither stents nor embolic coils are ideal treatment devices for wide neck aneurysms located at bifurcations.

A number of implant structures have been investigated for treating aneurysms located at bifurcations (such as disclosed in U.S. Pat. No. 10,004,510); however, there is an ongoing need for improved or alternative implant structures for treating aneurysms, particularly for treating wide neck aneurysms located at bifurcations.

SUMMARY

Embodiments presented herein include devices and implants for treating an aneurysm and methods for manufacturing and/or using the same. Implants described herein can be used as flow diverters and can generally include a plurality of twisting struts extending from a central node. The twisting struts can be twisted along a long axis of the strut. The implant can have a proximal portion affixed to the central node and extending radially from the central node. The twisting struts can have a distal portion. The long axis can be disposed between the proximal portion and the distal portion of the twisting struts. The twisting struts can have an interior surface. The twisting struts can have an exterior surface. The twisting struts can have an exterior spine. The implant can have a collapsed configuration to be delivered through a catheter into an aneurysm. The implant can have an expanded configuration to anchor within the aneurysm.

The central node can have a horizontal axis, and the proximal portion of the twisting struts can be affixed at an angle to the horizontal axis.

The central node can comprise a vertical axis. The twisting struts can be twisted about the vertical axis when the implant is in the collapsed configuration. This can aid in the delivery of the implant to and from the catheter. The twisting struts can be aligned and non-interleaved when the implant is in the expanded configuration. This can aid in the expansion of the implant into the aneurysm.

The interior surface of the distal portion of a twisting struts can contact the exterior surface of the distal portion of an adjacent twisting strut. This can aid the collapsing of the implant into the collapsed configuration.

The central node can have a plurality of angled steps. The angled steps can be affixed to one twisting strut.

The central node can be cylindrical. The proximal portion of each twisting strut can extend radially from the cylindrical central node.

The twisting struts can be expandable to extend into an aneurysm sac. The exterior spine of each twisting strut can be positioned to engage an aneurysm wall.

The implant can have a proximal stabilizing frame. The proximal stabilizing frame can be affixed to the central node and extend radially from the central node. The proximal stabilizing frame can engage a first blood vessel wall.

The proximal stabilizing frame can engage the first blood vessel wall in a first blood vessel branch. The proximal stabilizing frame can engage a second blood vessel wall in a second blood vessel branch The proximal stabilizing frame can have a first frame arm and a second frame arm. The first frame arm can engage the first blood vessel wall and the second frame arm can engage the second blood vessel wall. When the aneurysm is positioned at a bifurcation, the first frame arm and the second frame arm can extend opposite each other, and the first blood vessel wall can be at a first branch of the bifurcation, and the second blood vessel wall can be at a second branch of the bifurcation.

An example method for treating an aneurysm can include providing a flow diverter having a central node and a plurality of twisting struts. The central node can have a vertical axis. The twisting struts can have a proximal portion affixed to the central node and extending radially from the central node. The twisting struts can have a distal portion. The twisting struts can have a long axis between the proximal portion and the distal portion. The twisting struts can have an interior surface, an exterior surface, and an exterior spine. The method can include twisting the twisting struts along their long axis. The method can include twisting the twisting struts about the central node's vertical axis. The method can include delivering the flow diverter into an aneurysm treatment site, inserting the distal portion of the twisting struts into an aneurysm sac, and expanding the twisting struts to engage an aneurysm wall from within the aneurysm sac. Expanding the twisting struts can include untwisting the twisting struts from their position about the vertical axis and engaging the aneurysm wall at the exterior spine of the twisting struts. The method can include blocking an aneurysm neck with the flow diverter to divert a blood flow from the aneurysm to a blood vessel adjacent the aneurysm.

The flow diverter can have a proximal stabilizing frame affixed to the central node and extending radially from the central node. The method can include expanding the proximal stabilizing frame to engage a blood vessel wall.

The proximal stabilizing frame can include a first frame arm and a second frame arm. The step of expanding the proximal stabilizing frame can include engaging the first frame arm to a first blood vessel wall approximate the aneurysm neck in a first blood vessel branch. The step of expanding the proximal stabilizing frame can include engaging the second frame arm to a second blood vessel wall approximate the aneurysm neck in a second blood vessel branch.

An example method for loading a flow diverter into a catheter can include providing a flow diverter having a central node and a plurality of twisting struts. The central node can have a vertical axis. The twisting struts can have a proximal portion. The twisting struts can have a distal portion. The twisting struts can have a long axis between the proximal portion and the distal portion. The twisting struts can have an interior surface, an exterior surface, and an exterior spine. The method can include twisting each of the twisting struts along their long axis, setting a first predetermined distance from the distal portion of the twisting struts to an adjacent twisting strut, positioning the proximal portion of the flow diverter within a catheter, inserting the proximal portion of the flow diverter into the catheter, and moving the distal portion of the twisting struts from the first predetermined distance from the adjacent twisting strut to a second predetermined distance from the adjacent twisting strut. The second predetermined distance can be less than the first predetermined distance. The method can include interleaving the plurality of twisting struts. The step of interleaving the plurality of twisting struts can include twisting the twisting struts about the vertical axis of the central node and positioning the interior surface of the distal portion of the twisting struts upon the exterior surface of an adjacent twisting strut.

The flow diverter can have a proximal stabilizing frame affixed to the central node and extending radially from the central node. The method can include collapsing the proximal stabilizing frame to fit within the catheter.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 9B is a cutaway illustration of an exemplary aneurysm treatment device, having a proximal stabilizing frame, after being expelled from a catheter, according to the present invention;

FIG. 9C is a cutaway illustration of an exemplary aneurysm treatment device in a fully deployed configuration and having a proximal stabilizing frame engaging a vessel wall, according to the present invention;

FIG. 9D is a cross-section illustration of the implanted exemplary aneurysm treatment device of FIGS. 9A-9B viewed from the proximal end as indicated in FIG. 9C, according to the present invention;

FIGS. 10-13 are flow diagrams illustrating methods for treating an aneurysm, according to the present invention;

FIGS. 14-15 are flow diagrams illustrating methods for loading an exemplary aneurysm treatment device into a catheter, according to the present invention.

DETAILED DESCRIPTION

Figure 1:
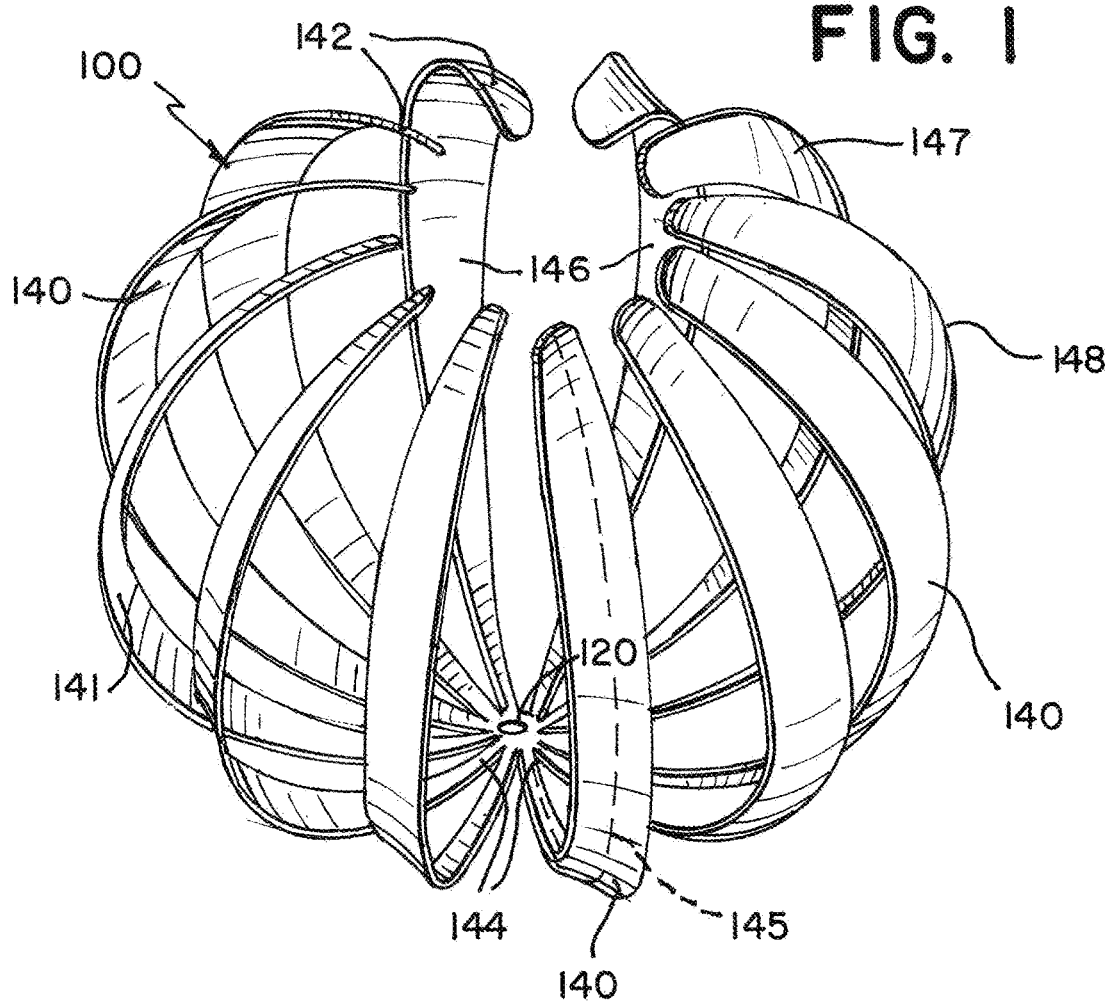
FIG. 1 is an illustration of an exemplary aneurysm treatment device, according to the present invention.

Flow diverters are endovasculature devices that direct blood flow away from an aneurysm. Most flow diverters treat side-wall aneurysms; however, many aneurysms occur at bifurcations. Example aneurysm treatment devices disclosed herein can include flow diverters implantable at a bifurcation and capable of anchoring in place with minimal intrusion into vasculature. It can be appreciated, however, that the aneurysm treatment devices described herein are not limited to being implanted at bifurcations. The devices described herein are capable of being employed within any aneurysm, including side-wall aneurysms.

Example devices herein can generally have a plurality of struts extending from a central node. Each strut can be formed with a slight twist along its long axis. This slight twist can facilitate a smooth retraction and deployment of the device into and from a catheter. For example, the slight twist along the long axis of each strut allows each of the plurality of twisted struts to interleave, thus avoiding edge-to-edge collision of the struts. In a device with multiple struts, the interleaving of the struts can provide uniform packing of the device into a catheter. The uniform packing of interleaved struts within a catheter can also prevent distortion of the final shape of the device once expelled from a catheter, thus helping to improve a deployed device's treatment effectiveness. Maintaining a proper final shape is important to the function of flow diverter devices, as the devices are designed to reside within an aneurysm sac and engage the interior walls of the aneurysm.

Example devices herein can have a proximal stabilizing frame. The proximal stabilizing frame can include one or more frame arms extending from the central node. The one or more frame arms can engage one or more vessel walls approximate an aneurysm neck. Engaging a vessel wall can stabilize the rotation of the device within the aneurysm sac. In any of the example devices herein, the device can be made from Nitinol or other shape memory material and formed into a sheet that is laser cut and shape set. For example, the struts, frame, node, and/or any other aspect or feature of the device can be made from Nitinol or any other shape memory material that can be deployed from a catheter and expand to a desired expanded configuration within an aneurysm sac.

Turning to the figures, as illustrated in FIGS. 1 through 9D, example aneurysm treatment devices can include a flow diverter with struts 100. A flow diverter with struts 100 can have a plurality of twisting struts 140 extending from a central node 120. Each twisting strut 140 can have a distal portion 142 and a proximal portion 144. The proximal portion 144 of the twisting struts 140 can be attached to the central node 120. Disposed between the proximal portion 144 and the distal portion 142 is a strut twist 141. The strut twist 141 is a twist along the long axis 145 of the twisting strut 140. This strut twist 141, as will be described in more detail below, allows the twisting struts 140 to interleave as they are collapsed into a collapsed configuration. The twisting struts can have a strut interior surface 146 and a strut exterior surface 147. These surfaces 146, 147 provide an area for a twisting strut 140 to rest upon an adjacent twisting strut 140. The twisting struts 140 can have an exterior spine 148 that engages an aneurysm wall when the flow diverter with struts 100 is expanded into an aneurysm 10.

FIG. 1 is a top-side perspective view illustration of an exemplary flow diverter with struts 100 in an expanded configuration. In some examples, this expanded configuration is exemplary of an implanted flow diverter with struts 100. As can be seen in the figure, a flow diverter with struts 100 can have a plurality of twisting struts 140 all extending radially from a central node 120. A flow diverter with struts 100 can have twelve twisting struts 140, as shown in the figure. However, any number of twisting struts 140 can be implemented within the devices. As will be appreciated by those having skill in the art, packing density within an aneurysm sac may be altered to achieve various attributes, such as durability of the device within the aneurysm and/or ability to embolize the aneurysm. Accordingly, the number of twisting struts 140 can be altered to achieve the desired attributes for a flow diverter with struts 100.

A flow diverter with struts 100 can have a strut twist 141 disposed between a proximal portion 144 and a distal portion 142 of each twisting strut 140. The strut twist 141 can help each of the twisting struts 141 to interleave as the flow diverter with struts 100 is collapsed to fit within a catheter. The strut twist 141 can lie between the proximal portion 144 and the distal portion 142 along a long axis 145 of each twisting strut 140. As shown in FIG. 1, each twisting strut 140 can increase in width along the long axis 145 from the proximal portion 144 to the distal portion 142. The twisting struts 140 can have a maximum width at a point between the proximal portion 144 and the distal portion 142, as shown in the figure. In some examples, the twisting struts 140 can have a maximum width at the proximal portion 144. In other examples, the twisting struts 140 can have a uniform width from the proximal portion 144 to the distal portion 142. A flow diverter with struts 100 can have an exterior spine 148 that, when the device is fully expanded and implanted, engages the wall of an aneurysm. Accordingly, the exterior spine 148 can be blunt, smooth, or similarly atraumatic so as to not perforate or tear the wall of an aneurysm.

Figure 2A:
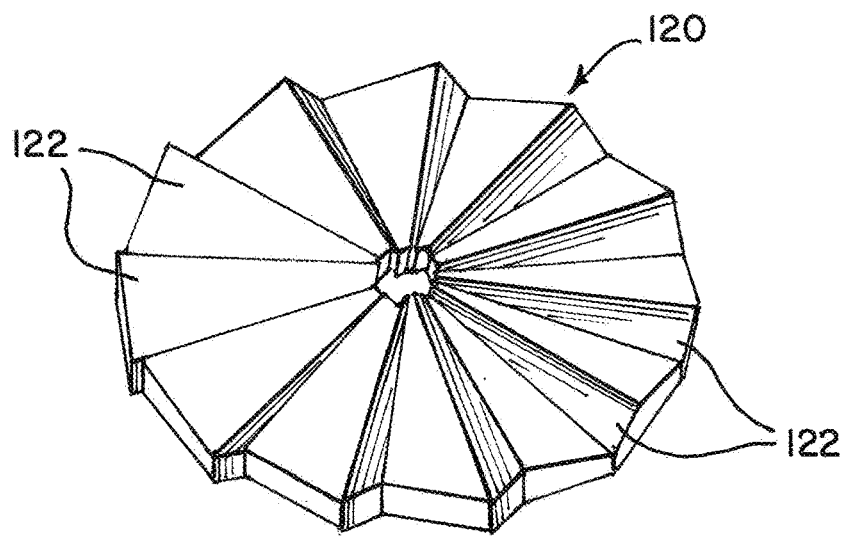
FIG. 2A is an illustration of an exemplary central node, according to the present invention.
Figure 2B:
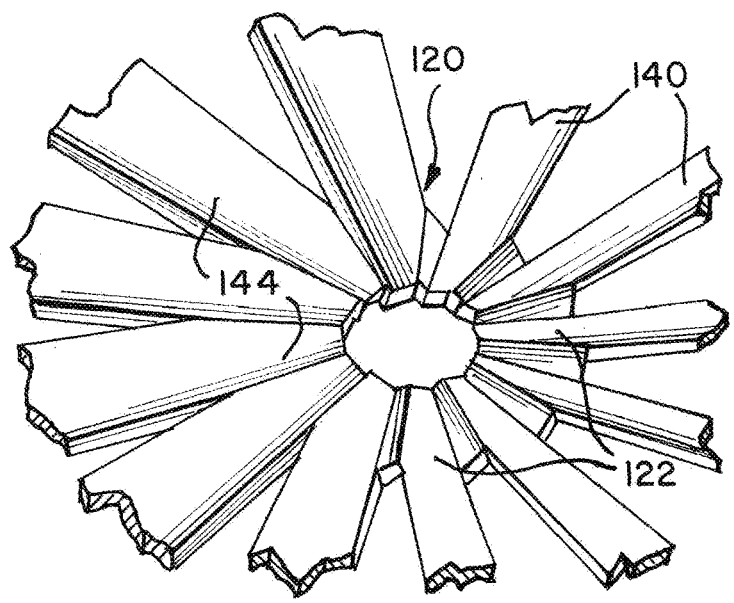
FIG. 2B is an illustration of an exemplary central node having angled steps and twisting struts extending radially, according to the present invention.

FIG. 2A is a perspective view of an exemplary central node 120. In some examples, the central node 120 can include a plurality of angled steps 122, as shown in the figure. In any example described herein, the central node 120 can be cannulated as shown, or the central node 120 can be solid. FIG. 2B shows a similar exemplary central node 120 to the one shown in FIG. 2A. In some examples, each angled step 122 can be affixed to the proximal portion 144 of one twisting strut 140, and each twisting strut 140 can extend radially from the central node 120 starting at the angle of the angled step 122.

Figure 2C:
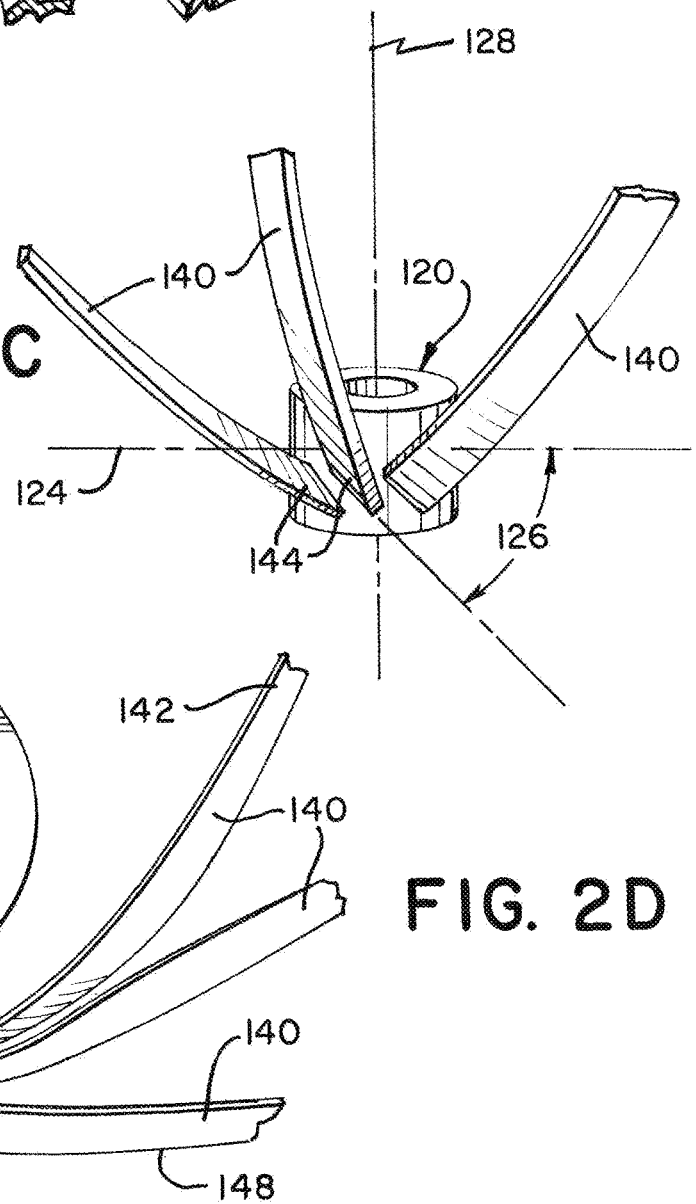
FIG. 2C is an illustration of an exemplary cylindrical central node with twisting struts extending radially, according to the present invention.

FIG. 2C is a perspective view illustration of an exemplary central node 120. In some examples, the central node 120 can be cylindrical, with each twisting strut 140 extending radially from the central node. In any example described herein, the central node 120 can have a node horizontal axis 124. The proximal portion 144 of the twisting struts 140 can be affixed to the central node 120 at an angle to the node horizontal axis 124. As will become apparent upon reading the disclosure in conjunction with the figures, this strut angle 126 can help facilitate the plurality of twisting struts 140 to twist together in a helical manner about a node vertical axis 128. This helical twisting about the vertical axis 128 aids the twisting struts 140 to interleave into a collapsed configuration to be packed within a catheter. The strut angle 126 between the connection of the proximal portion 144 and the node horizontal axis 124 can be any angle that facilitates the helical twisting of the twisting struts 140 about the vertical axis 128. The step angle 126 can be any angle between 0 degrees and 90 degrees. However, in some examples, in lieu of a strut angle 126 between the proximal portion 144 attachment and the node horizontal axis 124, the twisting struts 140 can extend either at 0 degrees or at 90 degrees to the node horizontal axis 124 and twist suddenly to create the twist needed for the helical twisting about the vertical axis 128. In the example central nodes 120 shown in FIGS. 2A and 2B, the strut angle 126 can be defined by the angle of the angled steps 122.

Figure 2D:
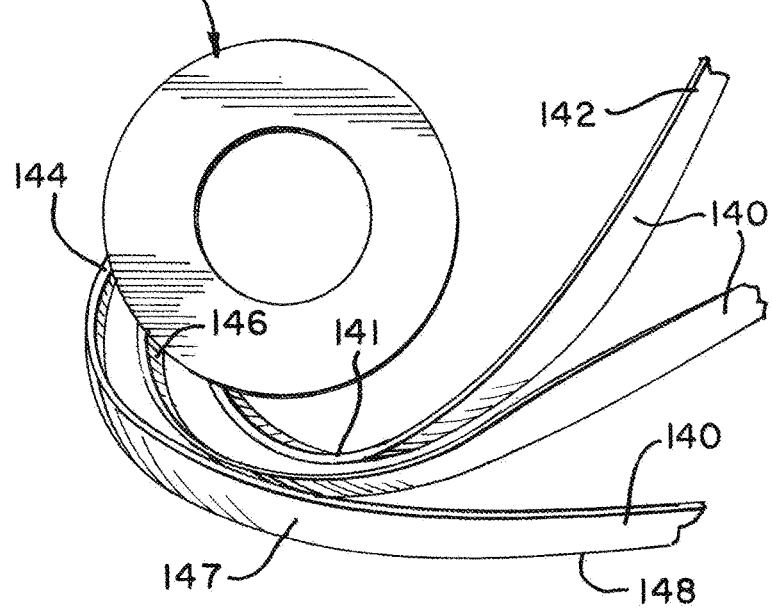
FIG. 2D is a top-view illustration of a central node showing the twist of twisting struts, according to the present invention.

FIG. 2D is a top view of an exemplary flow diverter with struts 100, showing helical twisting of the twisting struts 140. As described above, both the strut angle 126 (shown in FIG. 2C) and the strut twist 141 along the long axis of each twisting strut 140 facilitates an interleaving of the twisting struts 140 together when the flow diverter with struts 100 is collapsed into a collapsed configuration. FIG. 2D is an illustration of the interleaving that aids in packing the device into a catheter. In some examples, the interior surface of the distal portion 142 of a twisting strut 140 can contact the exterior surface 147 of the distal portion 142 of an adjacent twisting strut 140. This interleaving of each twisting strut 140 can create a section wherein each adjacent twisting strut 140 is packed neatly together, one exterior surface 147 resting on an adjacent interior surface 146.

Figure 3A:
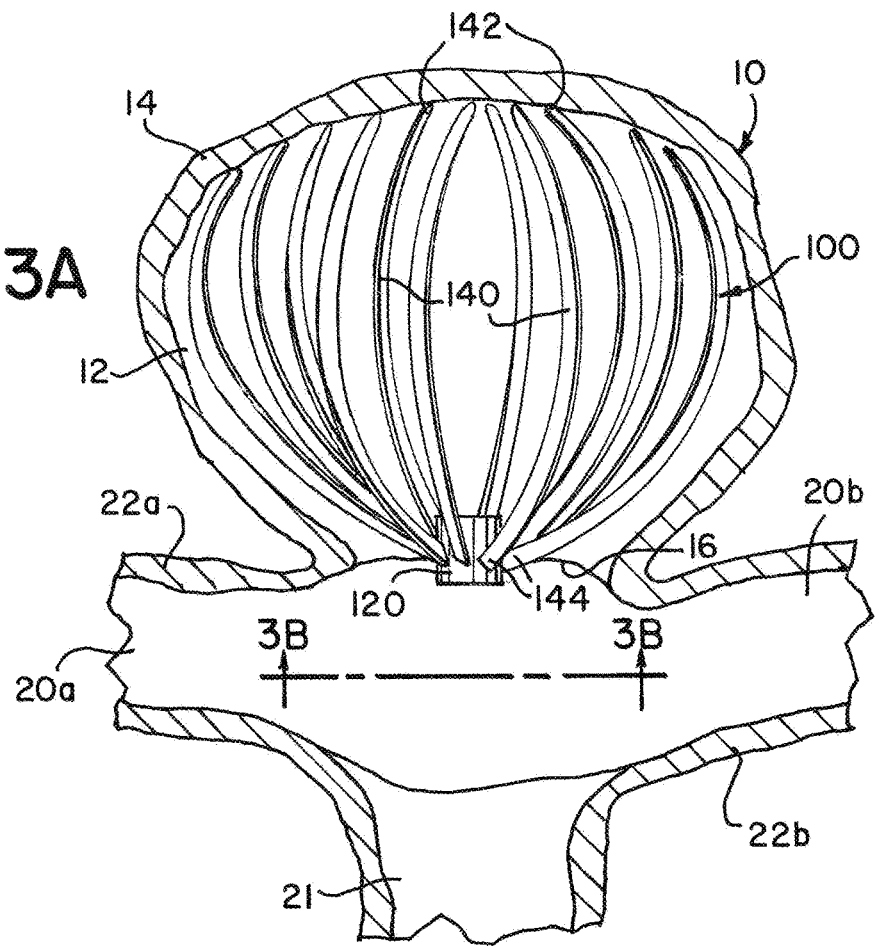
FIG. 3A is a cut-away illustration of an implanted exemplary aneurysm treatment device, according to the present invention.
Figure 3B:
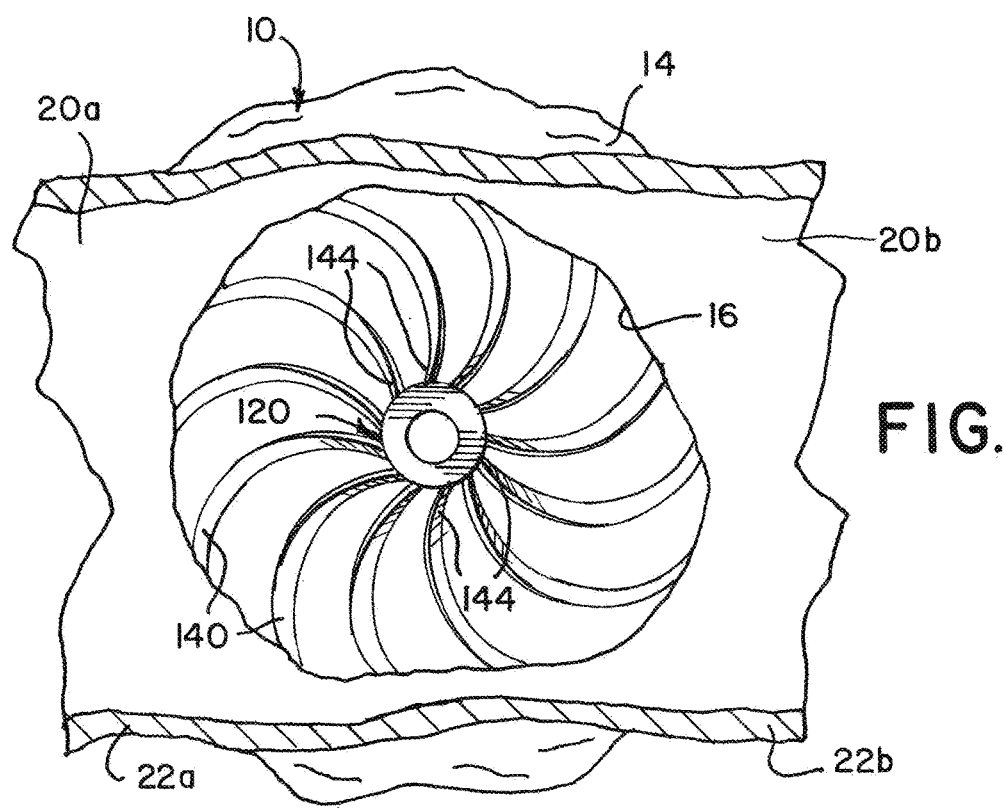
FIG. 3B is a cross-section illustration of the implanted exemplary aneurysm treatment device of FIG. 3A viewed from the proximal end as indicated in FIG. 3A, according to the present invention.

FIG. 3A is a cut-away illustration of an exemplary flow diverter with struts 100, according to the present invention. When implanted, the central node 120 can be positioned near the center of the aneurysm neck 16. The twisting struts 140 can extend distally from the central node 120 into the aneurysm sac 12. The twisting struts 140 can engage the aneurysm wall 14, thereby anchoring the device within the aneurysm 10. FIG. 3B is a is a cut-away illustration of the implanted exemplary aneurysm treatment device of FIG. 3A viewed from the proximal end, as indicated in FIG. 3A. The figure shows a central node positioned near the center of the aneurysm neck 16. In some examples, as the twisting struts 140 extend distally into the aneurysm sac 12 (not shown in FIG. 3B as it is distal to the current view), the contact between the twisting struts 140 and the aneurysm wall 14 prevents rotation of the device within the aneurysm sac 12. However, the spherical shape of the flow diverter with struts 100 does not require the central node 120 to be positioned at any particular position within the aneurysm neck 16. The packing density can remain the same even when the device rotates within the aneurysm.

Figure 4:
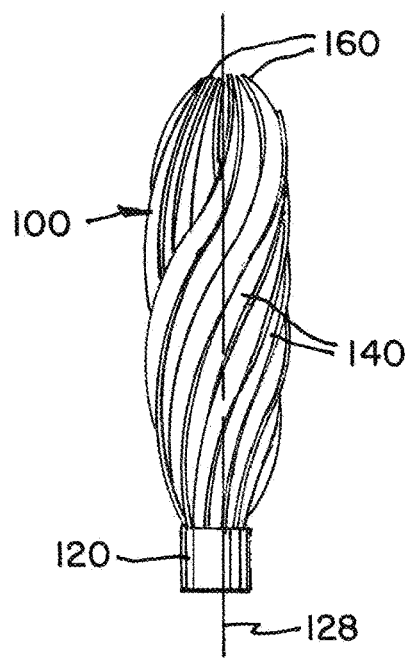
FIG. 4 is an illustration of exemplary aneurysm treatment device in a collapsed configuration, according to the present invention.

FIG. 4 is a side view of an exemplary flow diverter with struts 100 in a collapsed configuration. As described above, a flow diverter with struts 100 can have a collapsed configuration where the twisted struts 140 are twisted around the vertical axis 128 (as shown in FIG. 2C). This twisting around the vertical axis allows the twisting struts 140 to coil like a helix as they are collapsed into the collapsed configuration. This allows the struts to interleave as a set of interleaved struts 160. This interleaving avoids edge-to-edge collisions between each individual twisting strut 140 as the device is collapsed to fit within a catheter. This view of interleaved struts 160 in FIG. 4 is contrasted with the expanded configuration seen in FIGS. 1-3B, wherein the struts are aligned and non-interleaved. The interleaved struts 160 also promotes smooth retraction and deployment into and from a catheter.

Figure 5A:
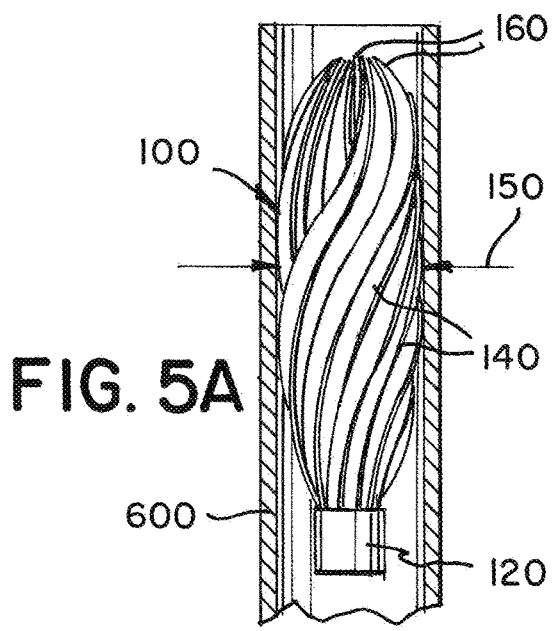
FIG. 5A is an illustration of an exemplary aneurysm treatment device in a collapsed configuration and loaded within a catheter, according to the present invention.

FIG. 5A is a cross-section illustration of an exemplary flow diverter with struts 100 in a collapsed configuration and loaded within a catheter 600. The exemplary flow diverter with struts 100 is sized for delivery though the catheter 600 and into a treatment site. This figure shows the benefits of a set of interleaved struts 160 in a collapsed configuration, where each twisting struts 140 is packed neatly together, one exterior surface (not shown in FIG. 5A) resting on an adjacent interior surface (not shown in FIG. 5A). The interleaved struts 160 create a uniform packing within the catheter 600, which aids in preventing a distortion of the final shape of the device. For example, and not limitation, the interleaving helps the twisting struts 140 maintain their curved and helical shape, such that when the device is retracted into a catheter 600 and deployed from the catheter 600, the curvature can remain and the twisting struts 140 can properly engage the interior walls 14 of the aneurysm.

The perimeter diameter of a collapsed flow diverter with struts 100 can depend first upon the inner diameter of the catheter 600 used in treatment and second upon the desired final perimeter diameter of a fully expanded flow diverter with struts 100. The collapsed perimeter diameter 150 refers to the outer diameter of a collapsed device as it rests within a catheter 600. As can be appreciated with a spherical-shaped flow diverter, the collapsed perimeter diameter 150 can be the diameter taken at the "widest" point on the collapsed device, which may be at the equator or elsewhere due to the collapsed nature of the device 100. The expanded perimeter diameter 152 of an expanded device (as seen in FIG. 5C) can again be measured at the equator, or the "widest" point of a non-uniformly shaped sphere. These dimensions can be in relation as the device 100 rests within the aneurysm 10. As will appreciated, the collapsed perimeter diameter 150 of the collapsed flow diverter with struts 100 should be less than the diameter of an aneurysm neck 16 (as shown in FIGS. 3A-3B). Also, the expanded perimeter diameter 152 of an expanded flow diverter with struts 100 should be substantially equal to the diameter of the aneurysm 10 from a first side of the aneurysm wall 14 to a second side approximately diametrically opposite the first side, as a substantially equal expanded perimeter diameter 152 can (i) prevent excess rotation of the device within the aneurysm 10 and (ii) prevent excess pressure upon the aneurysm wall 14. Therefore, if an exemplary aneurysm neck 16 is in the range of 1 mm to 20 mm, it is conceived that the collapsed perimeter diameter 150 of a collapsed flow diverter with struts 100 can be from between 1 mm and 20 mm. As will be appreciated, additional diameters of aneurysm necks 16 are possible, and thus additional ranges for a collapsed perimeter diameter 150 of a collapsed flow diverter with struts 100 are possible in the present invention. Also, if an exemplary aneurysm 10 has a diameter, from wall 14 to wall 14, in the range of 1 mm to 30 mm, it is conceived that the expanded perimeter diameter 152 of an expanded flow diverter with struts 100 can be from between 1 mm to 30 mm. As will be appreciated, additional diameters of an aneurysm 10 from wall 14 to wall 14 are possible, and additional ranges for an expanded perimeter diameter 152 of an expanded flow diverter with struts 100 are possible in the present invention.

Figure 5B:
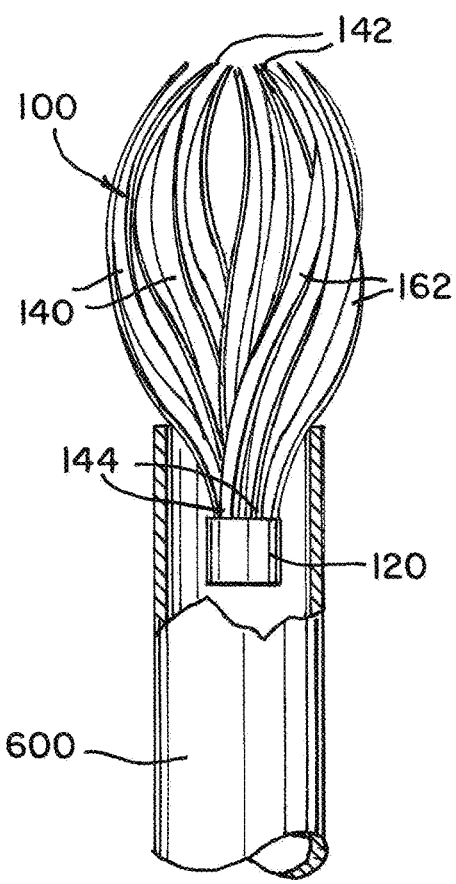
FIG. 5B is an illustration of an exemplary aneurysm treatment device partially expelled from a catheter, according to the present invention.
Figure 5C:
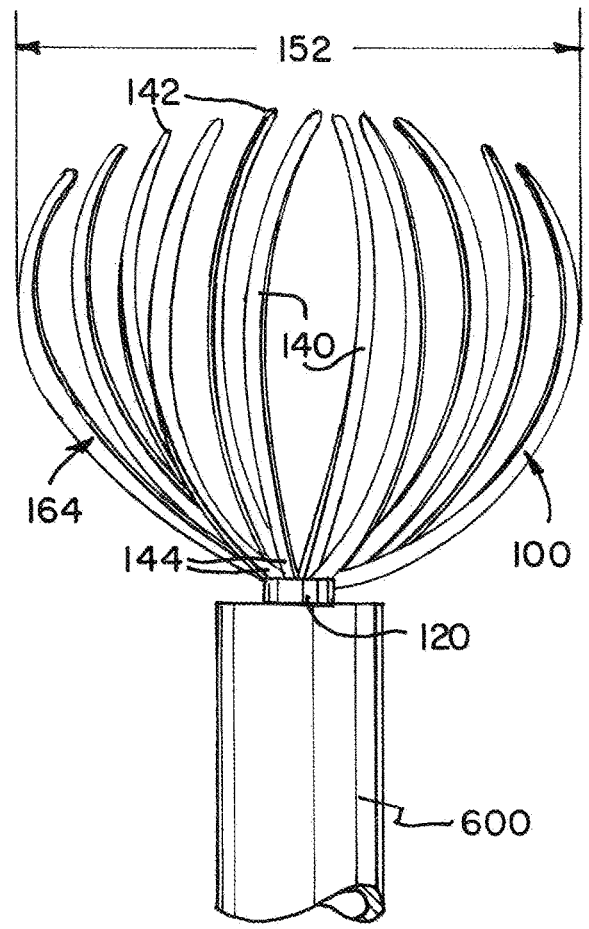
FIG. 5C is an illustration of an exemplary aneurysm treatment device fully expelled from a catheter, according to the present invention.

FIG. 5B is a cross-section view of an exemplary flow diverter with struts 100 partially expelled from a catheter 600. As shown in the figure, as the device is expelled from the catheter 600, the twisting struts 140 separate from each other slightly as they uncoil from their helical twisting about the vertical axis 128 (shown in FIG. 2C). As the device uncoils, a series of partially interleaved struts 162 can be disposed within the aneurysm 10. FIG. 5C is a perspective view of an exemplary flow diverter with struts 100 fully expelled from a catheter 600. This figure shows a device wherein the twisting struts 140 have expanded to their fully-expanded configuration, providing a device with non-interleaved, i.e., fully separated, struts 164.

Figure 6:
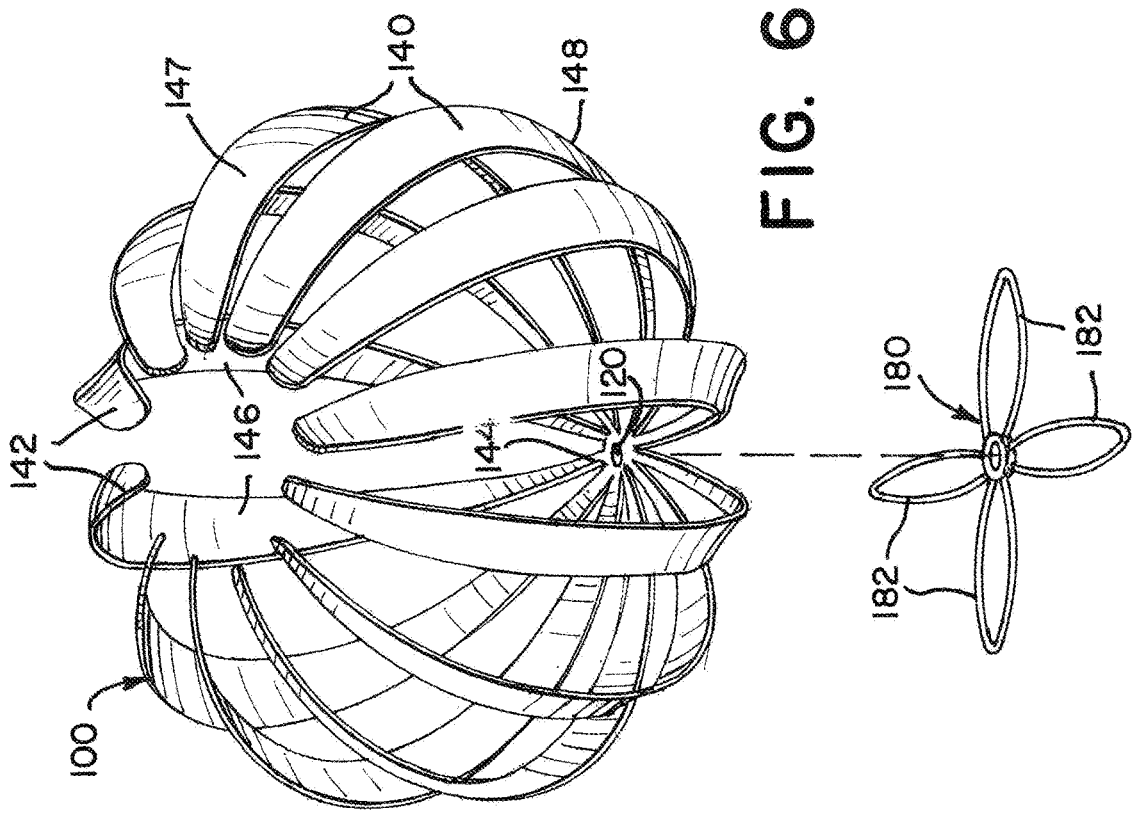
FIG. 6 is an exploded illustration of an exemplary aneurysm treatment device with a proximal stabilizing frame, according to the present invention.

FIG. 6 is a perspective, exploded view of an exemplary flow diverter with struts 100 with a proximal stabilizing frame 180. A flow diverter with struts 100 can have a proximal stabilizing frame 180 affixed to the central node 120. The proximal stabilizing frame 180 can extend radially from the central node 120 and engage one or more vessel walls exterior to the aneurysm sac, as will be shown in greater detail herein. The proximal stabilizing frame 180 can have one or more frame arms 182. The example illustration shows four frame arms 182, but the proximal stabilizing frame can have one, two, three, four, or more frame arms 182, depending on the site in which the device is to be implanted. The frame arms can extend radially from the central node 120 to engage blood vessel walls. The frame arms 182 can have a predetermined, or resting, shape. The predetermined shape can be a leaf, marquis, bar, or any other shape capable of extending into a vessel and engaging the vessel wall. The frame arms 182 of the proximal stabilizing frame 180 can be made from a memory shape material, for example and not limitation Nitinol, and the predetermined shape can be made by heat setting the proximal stabilizing frame 180 prior to loading the device into a catheter. The frame arms 182 of the proximal stabilizing frame 180 can be smooth or otherwise atraumatic along the surface that contacts the vessel wall. In some examples, the frame arms 182 can have additional features to aid in contact with a vessel wall, for example and not limitation, grippers, a roughened surface, or a widened surface.

Figure 7:
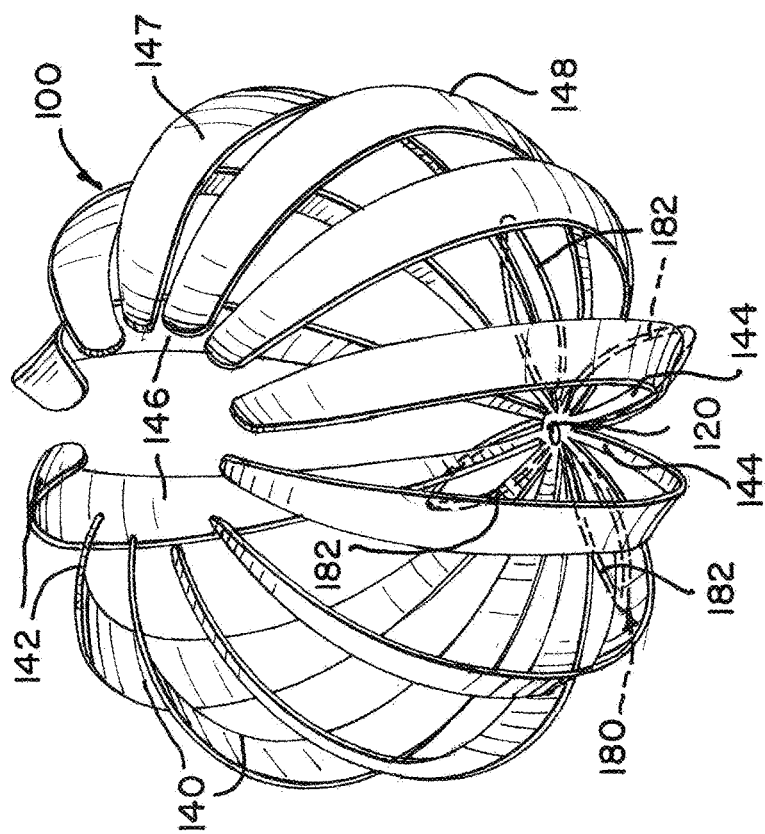
FIG. 7 is an illustration of an exemplary aneurysm treatment device with a proximal stabilizing frame, according to the present invention.

FIG. 7 is a perspective view illustration of an exemplary flow diverter with struts 100 with an attached proximal stabilizing frame 180. The figure shows the device in a fully expanded configuration. For example, the twisting struts 140 are separated from each other and the arms 182 of the proximal stabilizing frame 180 are expanded into their predetermined, expanded position.

Figure 8:
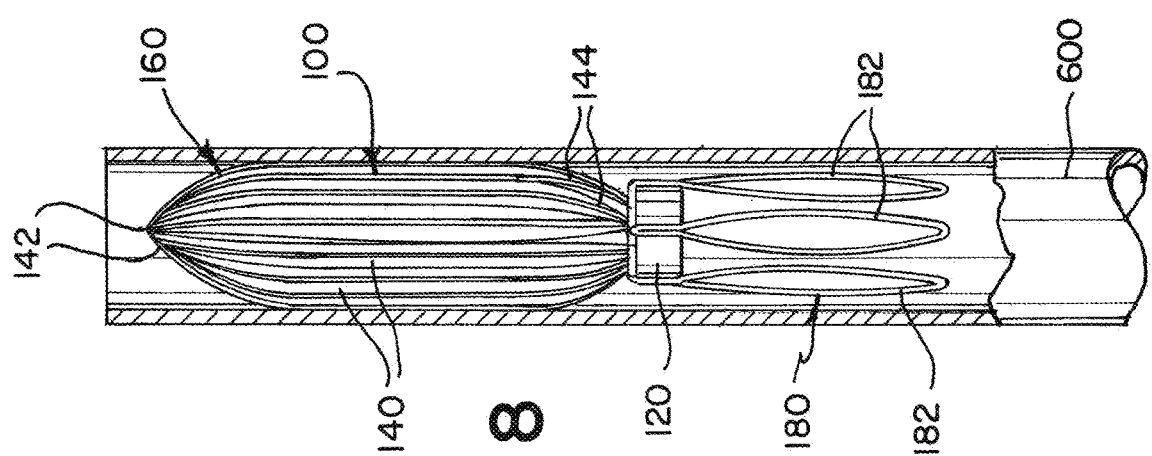
FIG. 8 is an illustration of an exemplary aneurysm treatment device, having a proximal stabilizing frame, in a collapsed configuration and loaded within a catheter, according to the present invention.

FIG. 8 is a cross-section view illustration of an exemplary flow diverter with struts 100, with a proximal stabilizing frame 180, in a collapsed configuration and loaded within a catheter 600. The exemplary flow diverter with struts 100 is sized for delivery though the catheter 600 and into a treatment site. The figure is similar to the embodiment shown in FIG. 5A, yet this example shows the device having a proximal stabilizing frame 180. A proximal stabilizing frame 180 can be collapsed into the loaded position, wherein the collapsing includes folding or bending the proximal stabilizing frame arms 182 down to fit within the catheter 600. This folding or bending can either be away from the twisting struts 140 or towards the twisting struts 140. Once the more distal portion of the device—the twisting struts 140 distal to the central node 120—are inserted into a treatment site, the frame arms 182 can follow to be positioned about vessel walls.

Figure 9A:
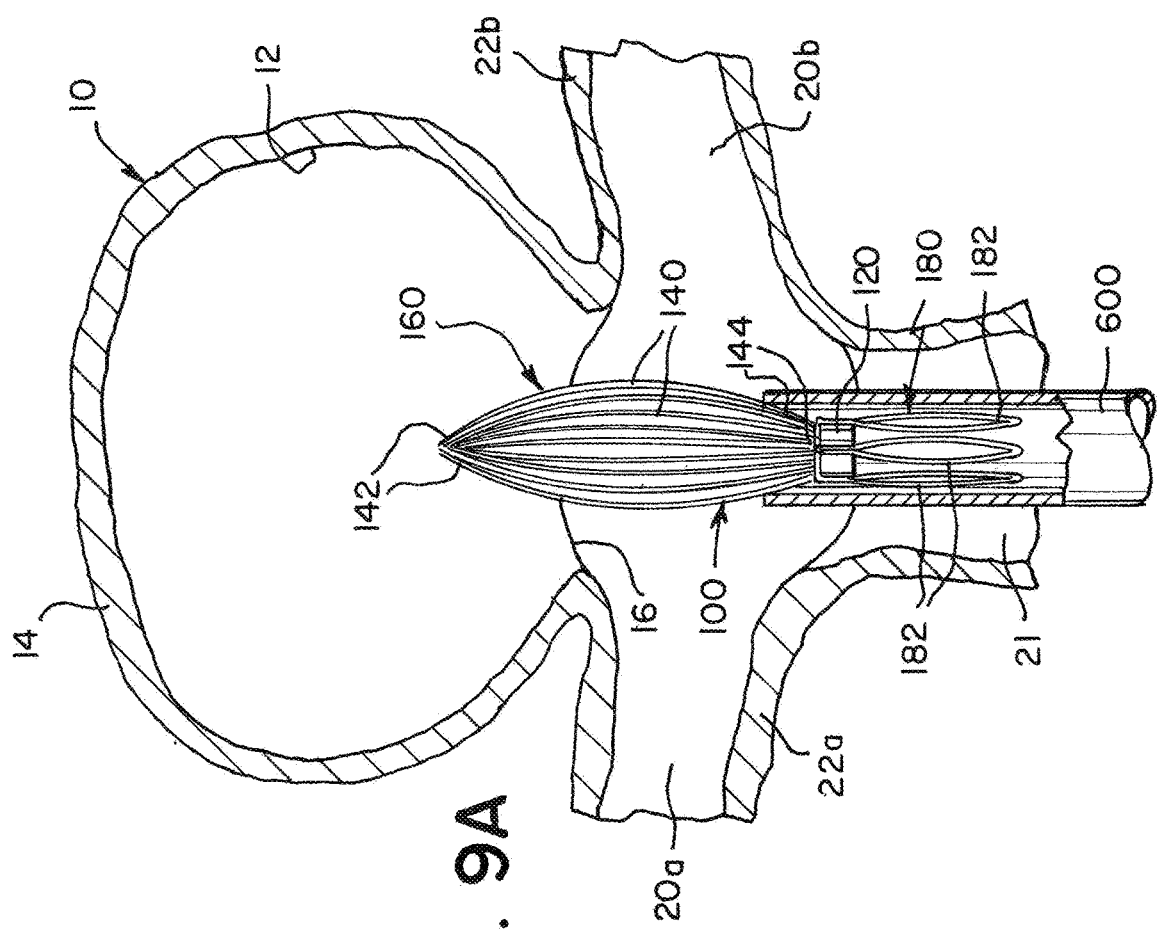
FIG. 9A is a cutaway illustration of an exemplary aneurysm treatment device, having a proximal stabilizing frame, being delivered to an aneurysm treatment site, according to the present invention.

FIG. 9A illustrates an exemplary flow diverter with struts 100, having a proximal stabilizing frame 180, being delivered to an aneurysm treatment site. As described above, the more distal portion of the flow diverter with struts 100 can first be delivered into an aneurysm 100 through the aneurysm neck 16. FIG. 9B is a cutaway illustration of an exemplary flow diverter with struts 100, having a proximal stabilizing frame 180, after being expelled from a catheter 600. As can be seen in the figure, the more distal portion of the device can engage the aneurysm walls 14 of the aneurysm 10 in a similar manner to the implanted configuration described in FIG. 3A. In a device with a proximal stabilizing frame 180, once the frame 180 has exited the catheter 600, the frame arms 182 of the proximal stabilizing frame 180 can extend from their loaded, folded state within the catheter 600 into their expanded, predetermined position.

FIG. 9C is a cutaway illustration of an exemplary flow diverter with struts 100, with a proximal stabilizing frame 180, in a fully deployed configuration, the frame arms 182 engaging vessel walls 22a,22b. The illustration in FIG. 9C shows how the invention described herein can be utilized at a bifurcation. For example, the stem blood vessel 21 meets at a bifurcation between a first blood vessel branch 20a and a second blood vessel branch 20b. The aneurysm 10 in this example is found at this bifurcation. As described above, however, the invention described herein is not limited to being implanted at a bifurcation. Once the device is implanted, the catheter 600 can be removed or repositioned as needed for further treatment. Additionally, the device 100 can also be retracted within the catheter 600 if needed. When being retracted, the proximal stabilizing frame 180 can collapse upwards towards the twisting struts 140, and the twisting struts 140 can twist helically around the vertical axis and interleave, as described here.

The example flow diverter with struts 100 in the FIG. 9C shows a plurality of frame arms extending from the central node 120. The frame arms 184a,184b (shown as frame arms 182 in FIGS. 6-7) of the proximal stabilizing frame 180 can extend radially from the central node 120 to engage a first blood vessel wall 22a in a first blood vessel branch 20a and a second blood vessel wall 22b in a second blood vessel branch 20b. Bifurcated vessels 20a,20b typically extend opposite each other from a stem blood vessel 21 as illustrated in FIG. 9C. Therefore, in this example, it can be advantageous for each frame arm 184a,184b to be positioned opposite the other to engage walls 22a,22b of blood vessel branches 20a,20b that are positioned opposite each other. Other anatomical geometries exist wherein blood vessel branches are not opposite, and it is contemplated that frame arms could be positioned at an angle with each other in an alternative design (not shown) to better engage blood vessel branches that are not opposite each other.

FIG. 9D illustrates the implanted exemplary flow diverter with struts 100 of FIGS. 9A-9B, viewed from the proximal end as indicated in FIG. 9C. As illustrated, the device can have four frame arms 182 extending from a central node 120. As shown, the frame arms 182 can be aligned such that two frame arms 182 extend into branch vessels 20a,20b and the other two frame arms 182 extend orthogonal to the branch vessels 20a,20b. Positioned thusly, the frame arms 182 extending into the branch vessels 20a,20b can be substantially straight when implanted, and the frame arms 182 can be curved when implanted to follow the curvature of the anatomy of the vasculature. Additionally, the frame arms 182 can be sized differently accounting for that there may be additional length needed to fully engage the branch vessels 20a,20b or less length for the diameter of the stem vessel 21. The differing sized frame arms 182 can have differing radiopaque markers to determine the size of each for particular placement in the patient.

It is contemplated that the device can have four frame arms 182 that are oriented at various rotational alignments in relation to the branch vessels 20a,20b, and it is not necessary for any of the frame arms 182 to align with the branch vessels 20a,20b in order to effectively stabilize the flow diverter with struts 100. For example, each frame arm 182 can be oriented at about 45° in relation to a branch vessel 20a,20b such that each frame arm 182 both extends into one of the branch vessels 20a,20b and curves to follow a curvature of the circumference of the respective branch vessel 20a,20b. It is contemplated that the frame arms 182 can be effective at stabilizing the flow diverter with struts 100 when implanted at any rotational orientation relative to the branch vessels 20a,20b. Having the option for multiple or infinite rotational alignments can make the flow diverter with struts 100 easier to position during implantation.

Although not shown, it is to be understood that example devices illustrated in FIGS. 1 through 5C can be implanted according to the principles and steps illustrated in FIGS. 6 through 9D. Also, it is to be understood that a flow diverter with struts 100 can be constructed and used by mixing and matching elements from the various examples. Any of the combinations of the features or shapes found in FIGS. 1 through 9D would be understood by a person of ordinary skill in the art.

FIGS. 10-13 are flow diagrams illustrating methods for treating an aneurysm. These method steps can be implemented by any of the example means described herein or by any means that would be known to a person of ordinary skill in the art.

Referring to method 700 as outlined in FIG. 10, in step 710, a flow diverter can be provided. The flow diverter can have a central node and a plurality of twisting struts extending from the central node. In step 720, the flow diverter can be delivered to an aneurysm treatment site. As descried herein the flow diverter can be delivered to an aneurysm treatment site via a catheter. The flow diverter can be loaded into the catheter in a collapsed configuration. The collapsed configuration includes twisting the twisting struts along their long axis, and twisting the twisting struts along the vertical axis, thereby creating the set of helical, interleaved struts. In step 730, the distal portion of the flow diverter can be inserted into an aneurysm sac of an aneurysm. In step 740, the twisting struts of the flow diverter can be expanded from their collapsed configuration to engage an aneurysm wall from within the aneurysm sac. The expanding of the twisting struts includes untwisting the twisting struts from their position about the vertical axis—or uncoiling their helical shape. In step 750, the expanded twisting struts engage the aneurysm wall at the exterior spine of the twisting struts. In step 760, the implanted device can divert a blood flow from the aneurysm to a blood vessel adjacent the aneurysm.

The method 700 illustrated in FIG. 10 can further include one or more of the steps outlined in FIG. 11. Referring to method 800 as outlined in FIG. 11, in step 810, a flow diverter with a proximal stabilizing frame can be provided. The flow diverter can have a proximal stabilizing frame attached at the central node and extending radially from the central node. In step 812, the proximal stabilizing frame can be expanded from a loaded position to engage one or more blood vessel walls, as described herein.

The methods 700 and 800 as illustrated in FIGS. 10 and 11 can further include one or more of the steps outlined in FIG. 12. Referring to method 814 as outlined in FIG. 12, in step 884, a flow diverter with a proximal stabilizing frame can have a first frame arm and a second frame arm. The first frame arm can be expanded from a loaded position to engage a first blood vessel wall approximate the aneurysm neck in a first blood vessel branch. In step 886, a second frame arm can be expanded from a loaded position to engage a second blood vessel wall approximate the aneurysm neck in a second blood vessel branch.

The method 700 illustrated in FIG. 10 can further include one or more of the steps outlined in FIG. 13. Referring to method 890 as outlined in FIG. 13, in step 892, the flow diverter can be implanted in an aneurysm positioned between bifurcated blood vessels opposite a stem blood vessel. In step 894, the implanted flow diverter can divert a blood flow from the stem blood vessel to the bifurcated vessel. In step 896, the implanted flow diverter can induce venous stasis in the aneurysm.

FIGS. 14-15 are flow diagrams illustrating methods for loading an exemplary flow diverter with struts 100 into a catheter 600. These method steps can be implemented by any of the example means described herein or by any means that would be known to a person of ordinary skill in the art.

Referring to method 900 as outlined in FIG. 14, in step 910, a flow diverter can be provided having a central node and a plurality of twisting struts extending from the central node. The flow diverter can be at an expanded configuration, wherein the twisting struts are separated from each other and not interleaved. At this expanded configuration, the distal portion of each twisting strut can be set to have a first predetermined distance from the distal portion of an adjacent twisting strut. This first predetermined distance can be determined and set based on the desired expanded shape of the device. In step 920, the proximal portion, near the central node, can be positioned within a catheter. In step 930, the flow diverter can be inserted into the catheter. In step 940, the twisting struts can be collapsed into a collapsed configuration to fit within the catheter. This collapsing can include moving the distal portion of each twisting strut from the first predetermined distance from the adjacent twisting strut to a second predetermined distance from the adjacent twisting strut, wherein the second predetermined distance is less than the first predetermined distance. In step 950, the collapsing includes interleaving the twisting struts. This interleaving of the twisting struts can include twisting the twisting struts about a vertical axis, or in other words, coiling the struts as a helix, as described herein. The interleaving can also include positioning the interior surface of the distal portion of each twisting strut upon the exterior surface of an adjacent twisting strut, thereby collapsing the device as it is inserted into the catheter.

The method 900 illustrated in FIG. 14 can further include one or more of the steps outlined in FIG. 15. Referring to method 960 as outlined in FIG. 15, in step 970, a flow diverter with a proximal stabilizing frame can be provided. The proximal stabilizing frame can be affixed to the central node and extend radially from the central node. In step 972, the proximal stabilizing frame can be collapsed to fit within a catheter. As described herein, the collapsing of the proximal stabilizing frame can include bending or folding the frame either proximal away from the twisting struts or towards the twisting struts. Additionally, as described herein, the proximal stabilizing frame can include one or more frame arms.

The descriptions contained herein are examples of embodiments of the invention and are not intended in any way to limit the scope of the invention. As described herein, the invention contemplates many variations and modifications of the device including using alternative geometries of structural elements, combining shapes and structural elements from various example embodiments, using alternative materials, etc. It is also contemplated that devices can be used to treat sidewall aneurysms, and examples are not intended to limit the application of the device to aneurysms that are positioned at a bifurcation or to treatment of wide necked aneurysms. These modifications would be apparent to those having ordinary skill in the art to which this invention relates and are intended to be within the scope of the claims which follow.

The invention claimed is:

1. A method comprising:
   providing a flow diverter comprising:
     a central node comprising a vertical axis and a plurality of angled steps, and
     a plurality of twisting struts extending from the central node, wherein each twisting strut of the plurality of twisting struts comprises:
       a proximal portion affixed to one angled step of the plurality of angled steps,
       a distal portion,
       a long axis disposed between the proximal portion and the distal portion,
       an interior surface, an exterior surface, and
an exterior spine,
twisting each twisting strut of the plurality of twisting struts along the long axis, and
setting a first predetermined distance from the distal portion of each twisting strut of the plurality of twisting struts to an adjacent twisting strut;
positioning a proximal portion of the flow diverter within a catheter;
inserting the proximal portion of the flow diverter into the catheter;
moving the distal portion of each twisting strut of the plurality of twisting struts from the first predetermined distance from the adjacent twisting strut to a second predetermined distance from the adjacent twisting strut, wherein the second predetermined distance is less than the first predetermined distance; and
interleaving the plurality of twisting struts, wherein interleaving the plurality of twisting struts comprises:
twisting each twisting strut of the plurality of twisting struts about the vertical axis; and
positioning the interior surface of the distal portion of each twisting strut of the plurality of twisting struts upon the exterior surface of an adjacent twisting strut.

2. The method of claim 1, wherein the flow diverter further comprises a proximal stabilizing frame affixed to the central node and extending radially from the central node, the method further comprising the step of collapsing the proximal stabilizing frame to fit within the catheter.

3. The method of claim 1 further comprising:
delivering the flow diverter to an aneurysm treatment site;
inserting the distal portion of the plurality of twisting struts into an aneurysm sac of an aneurysm; and
expanding the plurality of twisting struts to engage an aneurysm wall from within the aneurysm sac, wherein the expanding step comprises:
untwisting the plurality of twisting struts from their position about the vertical axis; and
engaging the aneurysm wall at the exterior spine of the plurality of twisting struts.

4. The method of claim 3 further comprising expanding a proximal stabilizing frame of the flow diverter to engage a blood vessel wall.

5. The method of claim 4,
wherein the proximal stabilizing frame comprises a first frame arm and a second frame arm, and
wherein the step of expanding the proximal stabilizing frame to engage the blood vessel wall comprises:
engaging the first frame arm to a first blood vessel wall approximate an aneurysm neck in a first blood vessel branch; and
engaging the second frame arm to a second blood vessel wall approximate the aneurysm neck in a second blood vessel branch.

6. A method comprising:
twisting a plurality of twisting struts along a vertical axis of a central node of a flow diverter, wherein each twisting strut of the plurality of twisting struts is connected to the central node at an angled step such that twisting the plurality of twisting struts causes the plurality of twisting struts to further twist about a long axis of each twisting strut;
collapsing the flow diverter by moving a distal portion of each twisting strut of the plurality of twisting struts from a first predetermined distance from an adjacent twisting strut to a second predetermined distance from the adjacent twisting strut, wherein the second predetermined distance is less than the first predetermined distance; and
interleaving the plurality of twisting struts, wherein interleaving the plurality of twisting struts comprises:
positioning an interior surface of the distal portion of each twisting strut of the plurality of twisting struts upon an exterior surface of an adjacent twisting strut.

7. The method of claim 6 further comprising inserting the flow diverter in a collapsed configuration into a catheter.

8. The method of claim 6 further comprising the step of collapsing a proximal stabilizing frame connected to the central node to fit within a catheter.

9. The method of claim 8, wherein, once collapsed, the proximal stabilizing frame extends in a direction opposite the plurality of twisting struts with respect to the vertical axis.

10. The method of claim 6 further comprising:
delivering the flow diverter to an aneurysm treatment site;
inserting the distal portion of the plurality of twisting struts into an aneurysm sac of an aneurysm; and
expanding the plurality of twisting struts to engage an aneurysm wall from within the aneurysm sac, wherein the expanding step comprises:
untwisting the plurality of twisting struts from their position about the vertical axis; and
engaging the aneurysm wall at an exterior spine of the plurality of twisting struts.

11. The method of claim 10 further comprising expanding a proximal stabilizing frame of the flow diverter to engage a blood vessel wall.

12. The method of claim 11,
wherein the proximal stabilizing frame comprises a first frame arm and a second frame arm, and
wherein the step of expanding the proximal stabilizing frame to engage the blood vessel wall comprises:
engaging the first frame arm to a first blood vessel wall approximate an aneurysm neck in a first blood vessel branch; and
engaging the second frame arm to a second blood vessel wall approximate the aneurysm neck in a second blood vessel branch.

13. A method comprising:
providing a flow diverter comprising:
a central node comprising a vertical axis comprising a plurality of angled steps; and
a plurality of twisting struts extending from the central node, wherein the plurality of twisting struts comprises:
a proximal portion affixed to one angled step of the plurality of angled steps,
a distal portion,
a long axis disposed between the proximal portion and the distal portion,
an interior surface,
an exterior surface, and
an exterior spine,
twisting each twisting strut of the plurality of twisting struts along the long axis;
twisting each twisting strut of the plurality of twisting struts about the vertical axis;
delivering the flow diverter to an aneurysm treatment site;
inserting the distal portion of the plurality of twisting struts into an aneurysm sac of an aneurysm; and
expanding the plurality of twisting struts to engage an aneurysm wall from within the aneurysm sac, wherein the expanding step comprises:

untwisting the plurality of twisting struts from their position about the vertical axis; and engaging the aneurysm wall at the exterior spine of the plurality of twisting struts.

14. The method of claim 13, wherein the flow diverter further comprises a proximal stabilizing frame affixed to the central node and extending radially from the central node, the method further comprising the step of expanding the proximal stabilizing frame to engage a blood vessel wall.

15. The method of claim 14, wherein the proximal stabilizing frame comprises a first frame arm and a second frame arm, and wherein the step of expanding the proximal stabilizing frame to engage the blood vessel wall comprises:

engaging the first frame arm to a first blood vessel wall approximate an aneurysm neck in a first blood vessel branch; and engaging the second frame arm to a second blood vessel wall approximate the aneurysm neck in a second blood vessel branch.

16. The method of claim 13, further comprising blocking an aneurysm neck with the flow diverter to divert a blood flow from the aneurysm to a blood vessel adjacent the aneurysm.

* * * * *